(12) United States Patent
Stack et al.

(10) Patent No.: US 9,827,130 B2
(45) Date of Patent: Nov. 28, 2017

(54) IMPLANTABLE DEVICES HAVING A RADIALLY EXPANDABLE BARRIER AND RELATED METHODS OF USE

(71) Applicant: Boston Scientific Scimed, Inc., Maple Grove, MN (US)

(72) Inventors: Richard S. Stack, Chapel Hill, NC (US); William L. Athas, Durham, NC (US); Richard A. Glenn, Chapel Hill, NC (US); Daniel Balbierz, Redwood City, CA (US); John Lunsford, San Carlos, CA (US); Michael S. Williams, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/150,784

(22) Filed: May 10, 2016

(65) Prior Publication Data
US 2016/0250055 A1    Sep. 1, 2016

Related U.S. Application Data

(60) Continuation of application No. 14/522,214, filed on Oct. 23, 2014, now Pat. No. 9,358,145, which is a continuation of application No. 13/236,431, filed on Sep. 19, 2011, now abandoned, which is a continuation of application No. 12/398,917, filed on Mar. 5, 2009, now Pat. No. 8,029,455, which is a division of application No. 10/345,666, filed on Jan. 16, 2003, now abandoned.

(51) Int. Cl.
*A61M 5/00*    (2006.01)
*A61F 5/00*    (2006.01)

(52) U.S. Cl.
CPC .......... *A61F 5/0079* (2013.01); *A61F 5/0036* (2013.01); *A61F 5/0076* (2013.01)

(58) Field of Classification Search
CPC ........ A61F 5/0079; A61F 5/0076; A61F 2/82; A61F 2/856
USPC ............ 604/8; 623/23.64, 23.68, 23.7, 23.67
See application file for complete search history.

(56) References Cited

U.S. PATENT DOCUMENTS

| | | |
|---|---|---|
| 5,314,473 A | 5/1994 | Godin |
| 5,486,187 A | 1/1996 | Schenck |
| 5,904,697 A | 5/1999 | Gifford et al. |
| 5,941,908 A | 8/1999 | Goldsteen et al. |
| 5,957,949 A | 9/1999 | Leonhardt et al. |
| 6,120,534 A * | 9/2000 | Ruiz ................ A61B 17/12109 606/194 |
| 6,146,416 A | 11/2000 | Andersen et al. |
| 6,187,020 B1 | 2/2001 | Zegdi et al. |
| 6,254,642 B1 * | 7/2001 | Taylor .................. A61F 2/0004 623/2.1 |

(Continued)

*Primary Examiner* — Alvin Stewart
(74) *Attorney, Agent, or Firm* — Bookoff McAndrews, PLLC (57) ABSTRACT

A method for controlling appetite by means of a satiation device is disclosed. The device, which includes a flexible webbing defining proximal and distal openings and a biasing structure, is attached to the patient's stomach with the proximal opening positioned adjacent and below the patient's gastro-esophageal junction. The biasing structure imparts pressure against the wall of the patient's stomach adjacent the gastro-esophageal junction.

13 Claims, 9 Drawing Sheets

(56) References Cited

U.S. PATENT DOCUMENTS

| | | | |
|---|---|---|---|
| 6,258,120 B1 * | 7/2001 | McKenzie | A61B 17/12109 606/200 |
| 6,264,700 B1 * | 7/2001 | Kilcoyne | A61F 2/04 623/23.68 |
| 6,302,917 B1 * | 10/2001 | Dua | A61F 2/04 623/23.64 |
| 6,558,429 B2 | 5/2003 | Taylor | |
| 6,675,809 B2 * | 1/2004 | Stack | A61F 2/04 128/898 |
| 6,764,518 B2 | 7/2004 | Godin | |
| 6,773,440 B2 | 8/2004 | Gannoe et al. | |
| 6,790,237 B2 | 9/2004 | Stinson | |
| 6,845,776 B2 | 1/2005 | Stack et al. | |
| 6,960,233 B1 | 11/2005 | Berg et al. | |
| 6,981,978 B2 | 1/2006 | Gannoe | |
| 7,025,791 B2 | 4/2006 | Levine et al. | |
| 7,087,088 B2 | 8/2006 | Berg et al. | |
| 7,097,665 B2 | 8/2006 | Stack et al. | |
| 7,111,627 B2 | 9/2006 | Stack et al. | |
| 7,121,283 B2 | 10/2006 | Stack et al. | |
| 7,122,058 B2 | 10/2006 | Levine et al. | |
| 7,141,071 B2 | 11/2006 | Imran | |
| 7,146,984 B2 | 12/2006 | Stack et al. | |
| 7,152,607 B2 | 12/2006 | Stack et al. | |
| 7,160,312 B2 | 1/2007 | Saadat | |
| 7,175,660 B2 | 2/2007 | Cartledge et al. | |
| 7,182,788 B2 | 2/2007 | Jung et al. | |
| 7,211,114 B2 * | 5/2007 | Bessler | A61F 2/07 623/23.65 |
| 7,220,237 B2 | 5/2007 | Gannoe et al. | |
| 7,220,284 B2 | 5/2007 | Kagan et al. | |
| 7,229,428 B2 | 6/2007 | Gannoe et al. | |
| 7,267,694 B2 | 9/2007 | Levine et al. | |
| 7,288,101 B2 | 10/2007 | Deem et al. | |
| 7,306,614 B2 | 12/2007 | Weller et al. | |
| 7,314,489 B2 | 1/2008 | McKenna et al. | |
| 7,316,716 B2 | 1/2008 | Egan | |
| 7,329,285 B2 | 2/2008 | Levine et al. | |
| 7,354,455 B2 | 4/2008 | Stinson | |
| 7,431,725 B2 | 10/2008 | Stack et al. | |
| 7,520,884 B2 | 4/2009 | Swanstrom et al. | |
| 7,594,885 B2 | 9/2009 | Byrum | |
| 7,601,178 B2 | 10/2009 | Imran | |
| 7,608,114 B2 | 10/2009 | Levine et al. | |
| 7,615,064 B2 | 11/2009 | Bjerken | |
| 7,628,821 B2 | 12/2009 | Stack et al. | |
| 7,766,954 B2 * | 8/2010 | Chobotov | A61F 2/07 623/1.13 |
| 7,766,973 B2 | 8/2010 | Levine et al. | |
| 7,789,848 B2 | 9/2010 | Gannoe et al. | |
| 7,833,280 B2 | 11/2010 | Stack et al. | |
| 7,837,669 B2 | 11/2010 | Dann et al. | |
| 7,846,138 B2 | 12/2010 | Dann et al. | |
| 7,846,174 B2 | 12/2010 | Baker et al. | |
| 7,892,292 B2 | 2/2011 | Stack et al. | |
| 7,981,162 B2 | 7/2011 | Stack et al. | |
| 7,993,410 B2 | 8/2011 | Shin et al. | |
| 8,029,455 B2 * | 10/2011 | Stack | A61F 5/0076 604/8 |
| 8,083,758 B2 | 12/2011 | Hsu et al. | |
| 8,100,931 B2 | 1/2012 | Baker et al. | |
| 8,177,853 B2 | 5/2012 | Stack et al. | |
| 8,182,543 B2 | 5/2012 | Schurr | |
| 8,187,297 B2 | 5/2012 | Makower et al. | |
| 8,206,456 B2 | 6/2012 | Stack et al. | |
| 8,211,050 B2 | 7/2012 | Kalanovic et al. | |
| 8,211,186 B2 | 7/2012 | Belhe et al. | |
| 8,241,202 B2 | 8/2012 | Balierz et al. | |
| 8,257,365 B2 | 9/2012 | Demarais et al. | |
| 8,267,888 B2 | 9/2012 | Marco et al. | |
| 8,282,598 B2 | 10/2012 | Belhe et al. | |
| 8,303,669 B2 | 11/2012 | Meade et al. | |
| 8,323,350 B2 | 12/2012 | Nissi | |
| 8,337,566 B2 | 12/2012 | Stack et al. | |
| 8,337,567 B2 | 12/2012 | Stack et al. | |
| 8,361,087 B2 | 1/2013 | Geitz | |
| 8,500,821 B2 | 8/2013 | Sobrino-Serrano et al. | |
| 8,529,431 B2 | 9/2013 | Baker et al. | |
| 8,597,366 B2 | 12/2013 | Shank | |
| 8,603,188 B2 | 12/2013 | Behan et al. | |
| 8,603,189 B2 | 12/2013 | Behan et al. | |
| 9,358,145 B2 * | 6/2016 | Stack | A61F 5/0076 |
| 2002/0032487 A1 | 3/2002 | Dua et al. | |
| 2002/0183768 A1 | 12/2002 | Deem et al. | |
| 2003/0009236 A1 * | 1/2003 | Godin | A61F 2/04 623/23.68 |
| 2003/0040808 A1 | 2/2003 | Stack et al. | |
| 2003/0060894 A1 | 3/2003 | Dua et al. | |
| 2003/0093117 A1 | 5/2003 | Saadat | |
| 2003/0109892 A1 | 6/2003 | Deem et al. | |
| 2003/0199987 A1 | 10/2003 | Berg et al. | |
| 2003/0220684 A1 * | 11/2003 | Holman | A61B 17/12045 623/1.21 |
| 2004/0039452 A1 | 2/2004 | Bessler | |
| 2004/0082963 A1 | 4/2004 | Gannoe et al. | |
| 2004/0107004 A1 * | 6/2004 | Levine | A61B 17/0401 623/23.64 |
| 2004/0117031 A1 | 6/2004 | Stack et al. | |
| 2005/0065614 A1 | 3/2005 | Stinson | |
| 2005/0096750 A1 | 5/2005 | Kagan et al. | |
| 2005/0143760 A1 | 6/2005 | Imran | |
| 2005/0149114 A1 | 7/2005 | Cartledge et al. | |
| 2005/0192599 A1 | 9/2005 | Demarais | |
| 2005/0228504 A1 * | 10/2005 | Demarais | A61B 17/12099 623/23.65 |
| 2005/0250980 A1 | 11/2005 | Swanstrom et al. | |
| 2005/0256587 A1 * | 11/2005 | Egan | A61F 5/0076 623/23.65 |
| 2006/0161172 A1 | 7/2006 | Levine et al. | |
| 2006/0217748 A1 | 9/2006 | Ortiz | |
| 2006/0241662 A1 | 10/2006 | Adams et al. | |
| 2006/0253142 A1 | 11/2006 | Bjerken | |
| 2006/0253144 A1 | 11/2006 | Mikkaichi | |
| 2007/0027549 A1 | 2/2007 | Godin | |
| 2007/0060932 A1 | 3/2007 | Stack et al. | |
| 2007/0129738 A1 | 6/2007 | Kraemer et al. | |
| 2007/0167962 A1 | 7/2007 | Gannoe et al. | |
| 2007/0175488 A1 | 8/2007 | Cox et al. | |
| 2007/0276432 A1 | 11/2007 | Stack et al. | |
| 2007/0293716 A1 | 12/2007 | Baker et al. | |
| 2008/0172072 A1 | 7/2008 | Pool et al. | |
| 2008/0243151 A1 | 10/2008 | Binmoeller et al. | |
| 2009/0012542 A1 | 1/2009 | N'diaye et al. | |
| 2009/0024143 A1 | 1/2009 | Crews et al. | |
| 2010/0204719 A1 | 8/2010 | Balbierz et al. | |
| 2010/0228272 A1 | 9/2010 | Balbierz et al. | |
| 2011/0190796 A1 | 8/2011 | Kraemer et al. | |
| 2011/0213389 A1 | 9/2011 | Geitz et al. | |
| 2011/0245854 A1 | 10/2011 | Buxbaum et al. | |
| 2012/0004590 A1 | 1/2012 | Stack et al. | |
| 2012/0089236 A1 | 4/2012 | Errico et al. | |
| 2012/0165955 A1 | 6/2012 | Geitz | |
| 2012/0296354 A1 | 11/2012 | Hsu et al. | |
| 2013/0023727 A1 | 1/2013 | Balbierz et al. | |
| 2013/0274772 A1 | 10/2013 | Kim et al. | |
| 2014/0114433 A1 | 4/2014 | McHugo | |
| 2014/0195006 A1 | 7/2014 | Treacy et al. | |

* cited by examiner

IMPLANTABLE DEVICES HAVING A RADIALLY EXPANDABLE BARRIER AND RELATED METHODS OF USE

This patent application is a continuation of U.S. patent application Ser. No. 14/522,214, filed Oct. 23, 2014, which is a continuation of U.S. patent application Ser. No. 13/236,431, filed Sep. 19, 2011 (now abandoned), which is a continuation of U.S. patent application Ser. No. 12/398,917, filed Mar. 5, 2009 (now U.S. Pat. No. 8,029,455, issued Oct. 4, 2011), which is a divisional of U.S. patent application Ser. No. 10/345,666, filed Jan. 16, 2003 (now abandoned). The entirety of each of the above-referenced applications is incorporated herein by reference.

FIELD OF THE INVENTION

The present invention relates generally to the field of devices and methods for achieving weight loss in humans, and specifically to the use of devices implantable within the human stomach for controlling feelings of hunger and/or limiting food intake.

BACKGROUND OF THE INVENTION

Figure 1A:
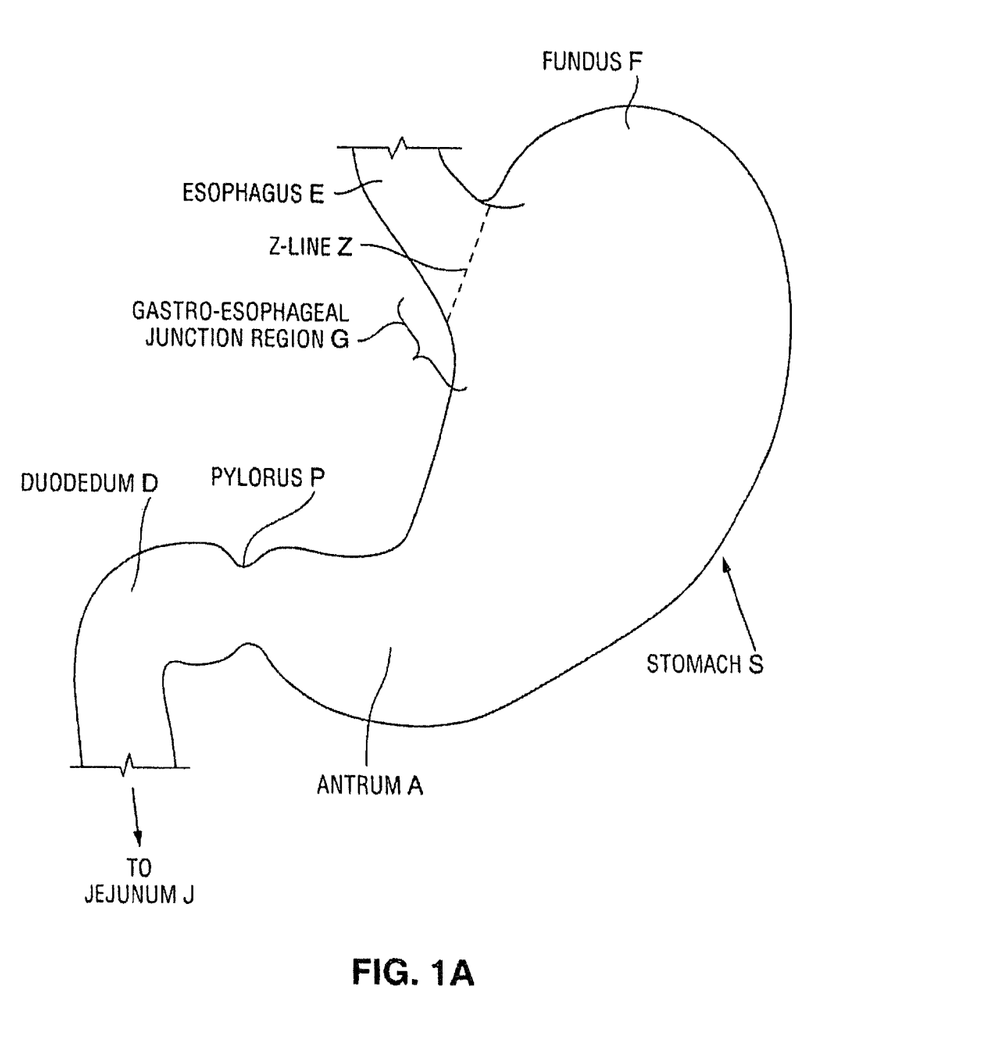
FIG. 1A is a schematic illustration of a human stomach and a portion of the small intestine.

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Figure 1B:
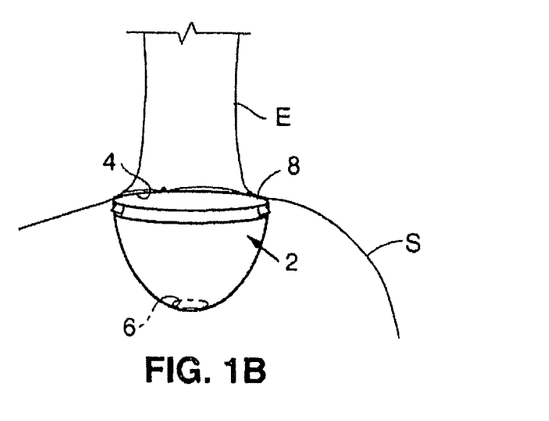
FIG. 1B is a perspective view of a satiation pouch provided without supplemental barrier features. The pouch is shown positioned in the stomach.

Prosthetic devices for use in controlling obesity are shown and described in U.S. application Ser. No. 09/940,110, filed Aug. 27, 2001 and U.S. application Ser. No. 10/118,289 filed Apr. 8, 2002, and U.S. Provisional Application No. 60/379,306 filed May 10, 2002. These applications are owned by the assignee of the present application, and the disclosures of these applications are incorporated herein by reference. Certain forms of these devices involve positioning a prosthetic pouch in the proximal stomach as shown in FIG. 1B. The pouch 2 includes a proximal opening 4 and a smaller distal opening 6 and forms a small reservoir that collects masticated food from the esophagus—thereby limiting the amount of food that can be consumed at one time. As the pouch fills with food, it may distend, imparting pressure against the upper stomach and lower esophageal sphincter causing the patient to experience sensations of fullness. The pouch may additionally or alternatively act as a restrictor, limiting the amount of food intake. The pouch is fixed in place using clips, sutures, suitable adhesives or other means 8 at anchor points around the perimeter of the proximal opening 4.

Figure 1C:
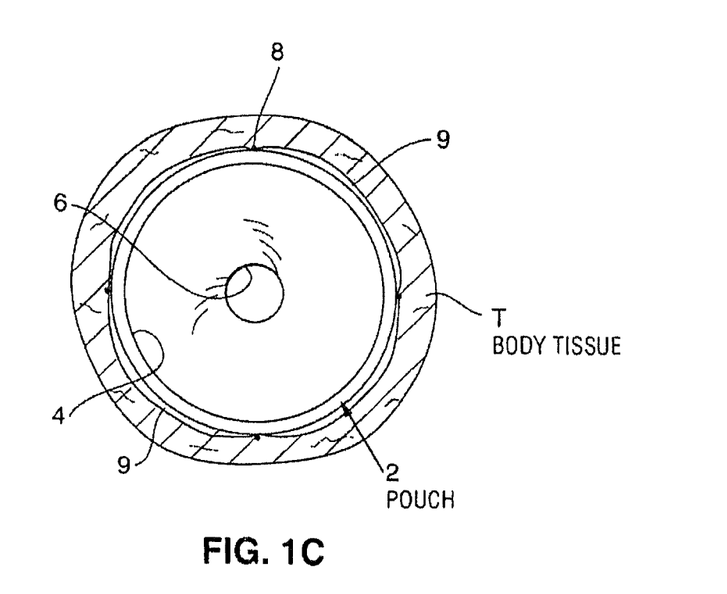
FIG. 1C is a top plan view of the satiation pouch of FIG. 1B shown within the stomach, and illustrating formation of gaps around the perimeter of the proximal opening.

Because of the flexible nature of the tissue of the gastro-esophageal junction region and/or the material forming the pouch, gaps 9 can occur along the perimeter of the pouch in regions between neighboring anchor points. Solving this problem is made more difficult by the flared geometry of the walls of the proximal stomach. Food entering or accumulating in the pouch 2 can ooze from these gaps and pass around the exterior of the pouch directly into the stomach, thereby decreasing the effectiveness of the prosthesis. The embodiments described herein optimize the function of the pouch devices by forming a barrier against passage of food through any such gaps and/or by eliminating such gaps.

SUMMARY OF THE INVENTION

The present invention includes a prosthetic device positionable within the gastro-esophageal junction region of a patient, wherein the prosthetic device includes a proximal opening and a barrier device defining a central passage at least partially aligned with the proximal opening of the prosthetic device. In a method for positioning the prosthetic device, the prosthetic device is attached to tissue of the gastro-esophageal region of the patient, with the device positioned such that food ingested by the patient passes from the esophagus through the central passage and proximal opening into the interior of the prosthetic device. The barrier contacts surrounding tissue and thereby minimizes passage of food from the esophagus around the exterior of the prosthetic device. In preferred forms of the embodiment, the barrier is adaptable in response to movement of the surrounding tissue to maintain contact between the barrier and the surrounding tissue.

DETAILED DESCRIPTION OF THE DRAWINGS

The drawings show a number of embodiments of satiation pouches having features that create a barrier against passage of food through gaps occurring between the upper perimeter of the pouch and adjacent tissue and/or that minimize or eliminate such gaps. Ideally, the barriers will form a seal with the adjacent tissue, however it is sufficient that the barriers prevent a substantial amount of food from passing between the exterior of the pouch and adjacent tissue, without necessarily forming an impermeable seal.

For the purposes of this application, the term "satiation devices" or "satiation pouches" will be used to mean devices or pouches intended to induce weight loss in one or more of a variety of ways. These include, but are not limited to, physically restricting the amount of food that can be consumed, and/or imparting pressure against portions of the body (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body.

The pouch of each described embodiment may be formed of a flexible material that will prevent passage of food through the sides of the pouch. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The material may be a composite of compliant, semi-compliant and/or non-compliant materials that give different regions of the pouch different degrees of compliance so as to allow/limit expansion of the pouch in various locations. For example, it may be desirable to provide the pouch with a fairly elastic exit port to as to prevent occlusion in the event a large piece of food is ingested and/or to control the exit pressure of food from the pouch, whereas the proximal end of the pouch may be stiffer to prevent bulging. Varying degrees of compliance may also be built into the pouch by varying the cross-sectional thickness in different regions of the pouch. The material may be coated with a lubricious, bio-compatible, chemically inert material, such as para-leyne, to reduce friction on the base material's surface which will help prevent sticking and food build up on the device. The flexible pouch material may be reinforced with, constructed of, or supported by supporting members, such as a soft mesh, a cage structure, ribs, rings etc. The supporting members may be formed of stainless steel, polymer, shape memory materials such as nitinol, shape memory alloys, or shape memory polymers, or thickened regions of material. The pouch may be constructed so as to be self-expanding, such that the pouch springs radially open into an expanded condition upon ejection from a deployment device or catheter.

Implantation of the described devices is preferably performed endoscopically, by passing the devices through the esophagus, preferably under endoscopic visualization. Alternatively, the devices may be implanted using surgical or laparoscopic procedures.

During implantation the pouch is secured at the gastroesophageal junction region G using sutures, clips, adhesives, stents or stent-like structures, or other suitable means. One suture attachment device found useful for applying sutures between the pouch and tissue is the "Sew-Right" suturing device available from LSI Solutions of Victor, N.Y. Although the pouch may be secured to the esophageal tissue, it is more preferable to apply sutures/clips below the Z-line to allow for attachment to the thicker tissue of the stomach wall.

Each of the described pouches includes a proximal opening and a distal exit port (see openings 4 and 6, respectively, of FIG. 1B). Because of its small volume (which may be on the order of approximately 2 cc-300 cc in volume, but is preferably in the range of 10-30 cc), the pouch functions to limit the amount of food that can be consumed at one time. Over time the food within this reservoir descends into the stomach through the exit port.

First Embodiment

Figure 2:
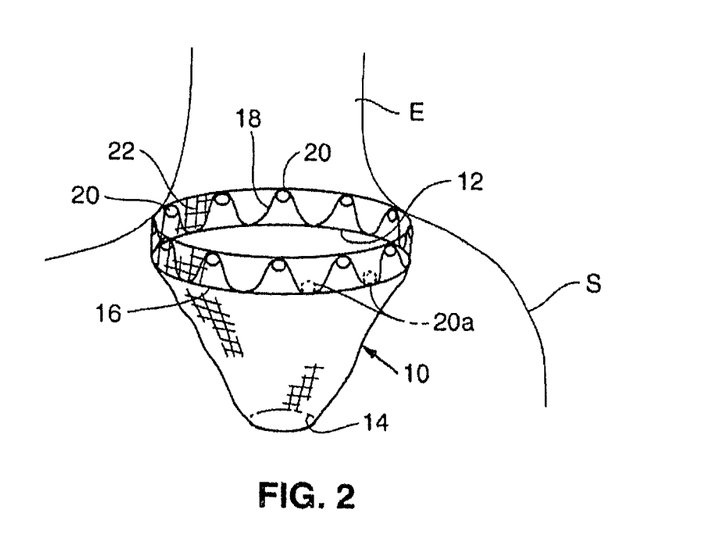
FIG. 2 is a perspective view of a first embodiment of a pouch having a circumferential barrier. The pouch is shown positioned in the stomach.
Figure 3:
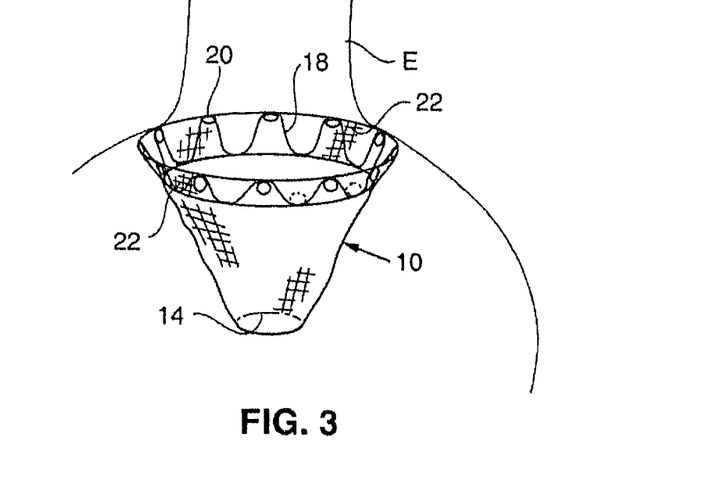
FIG. 3 is a perspective view similar to FIG. 2 showing expansion of the barrier into contact with tissue in a stomach having relatively broad proximal dimensions.

FIGS. 2 and 3 show a first embodiment of a pouch 10 having a proximal opening 12, distal exit port or opening 14 and a passage extending between the proximal and distal openings.

A resilient ring 16 surrounds the proximal opening 12 and a plurality of spring members 18 are attached to the ring 16. Spring members 18 are preferably biased in a radially outward direction and can pivot relative to ring 16. Although spring members 18 are preferably moveable independently of one another, they may take the form of multiple fingers formed along a single length of wire.

Anchor loops 20 are positioned on the spring members 18. The anchor loops 20 serve to receive sutures, clips or other attachment devices used to connect the pouch to surrounding tissue. The loops in each of the embodiments described in this application should be considered optional, since the pouch may alternatively be anchored directly to the tissue without the use of the loops 20.

The anchor loops 20 may be positioned in the outer apexes of the spring members as shown, and/or they may be positioned elsewhere such as closer to the ring 16. See, for example, loops 20a shown in dashed lines in FIG. 2. Ring 16, spring members 18 and loops 20 are preferably made of a resilient material (e.g. stainless steel, polymers etc.) suitable for use within the body.

Webbing 22 is connected to the spring members 18 along the circumference of the ring 16 to form a skirt-like member having a central opening. Webbing 22 is preferably formed of a flexible material that is substantially impermeable to masticated food. The material may be inelastic or elastic.

Examples of suitable materials for the webbing 22 include those listed above for use with the pouch. When the pouch is secured within a patient, the webbing forms a barrier against passage of food between the pouch and surrounding tissue, and directs food into the proximal opening of the pouch. The webbing 22 and spring members 18 are preferably configured to form a dynamic seal with the surrounding tissue, so as to maintain a substantially consistent barrier despite stomach movement and flexure of the pouch. For example, the webbing 22 may be made expandable by using an elastic material and/or by including pleats in the webbing that allow for expansion. Also, the spring members 18 are preferably independently moveable and thus contribute to the dynamic nature of the barrier. In one variation on the first embodiment, the ring 16 and/or spring members 18 may be eliminated and the material of the webbing 22 itself may provide the necessary spring properties. In such an example, both the pouch and webbing, or the webbing along, may be formed of a resilient silicone or other resilient material.

During use, pouch 10 is introduced into the stomach S via the esophagus E and is held in the desired attachment location in the gastro-esophageal junction region. The pouch is anchored in place such as by connecting sutures or other attachment means to plurality of the anchor loops 20/20a or directly to the pouch and/or webbing to secure the pouch 10 in position. The outward radial forces of spring members 18 cause the spring members 18 to extend radially outwardly, carrying the webbing 22 into contact with the surrounding tissue, creating a barrier that minimizes passage of food around the pouch. If required by the anatomy of the patient's stomach, the spring members 18 will cause the webbing 22 to flare outwardly into contact with the surrounding tissue as shown in FIG. 3. Similarly, a narrower proximal stomach may restrict outward movement of the spring members 18 such that they angle the webbing in a slight inward direction.

Figure 4A:
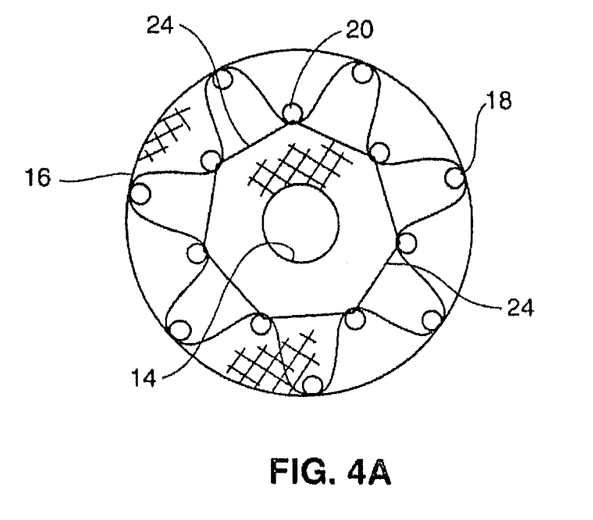
FIG. 4A is a top view of a pouch similar to the pouch of FIG. 2 showing the barrier and spring members restrained in a radially inward orientation.
Figure 4B:
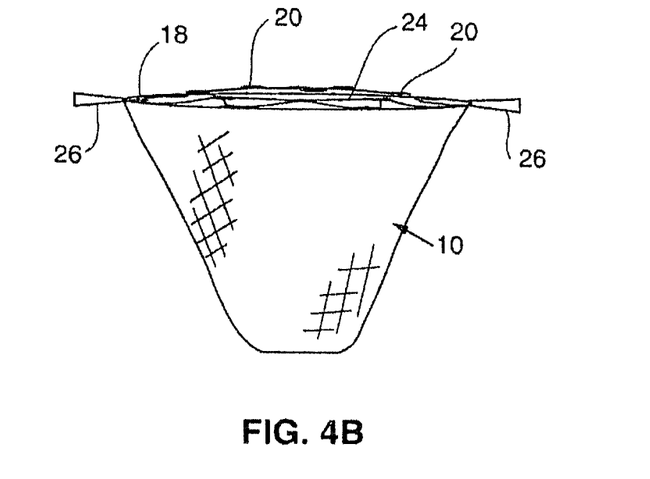
FIG. 4B is a side elevation view of the pouch of FIG. 4A.

If desired, the spring members 18 may be held in a laterally inward position as shown in FIGS. 4A and 4B during positioning of the pouch within the stomach. For example, temporary sutures 24 may be threaded through loops 20 and cinched to draw spring members 18 into the position shown in FIG. 4A. As illustrated in FIG. 4B, when drawn inwardly the spring members 18 and webbing 22 may have a relatively flat profile. The pouch may be anchored into position with the spring members 18 and pouch in the inward position, such as by attaching sutures to the loops 20 as described above, or by attaching sutures to additional anchor loops 26 that are separate from the spring members 18. Once the pouch has been sutured into place, temporary sutures 24 are snipped so as to release spring members 18, allowing the spring members 18 to carry the webbing into contact with the surrounding tissue.

Second Embodiment

Figures 5, 6:
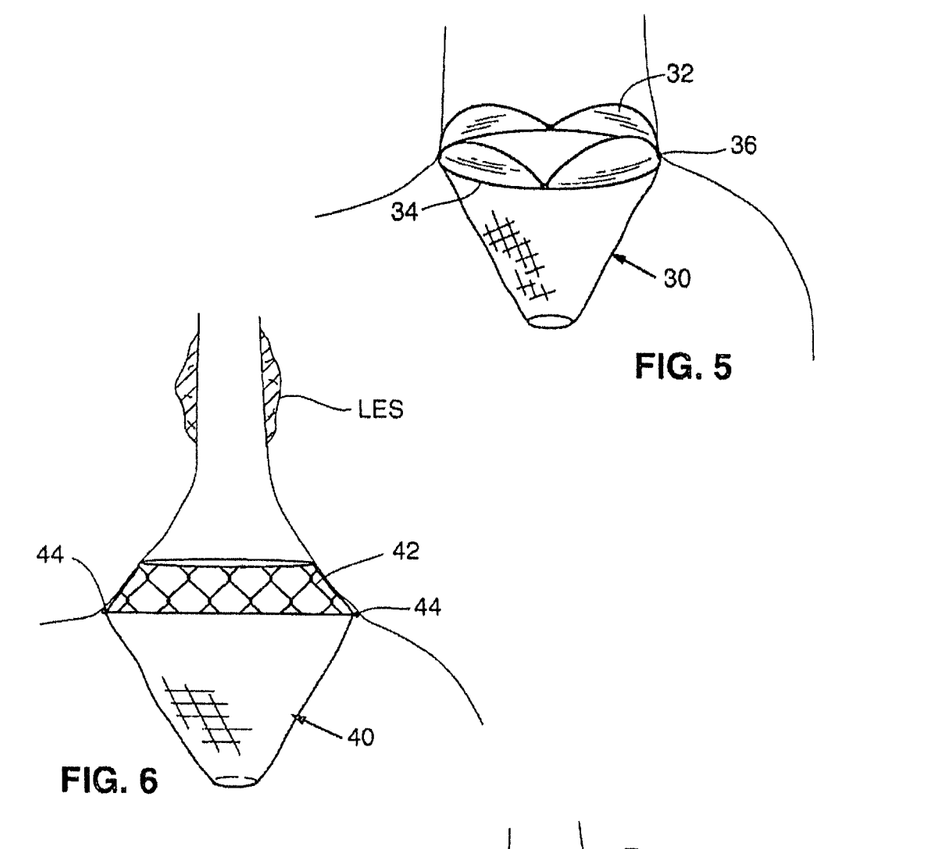
FIG. 5 is a perspective view similar to FIG. 2 showing a second embodiment having an alternative barrier configuration utilizing blade members.
FIG. 6 is a perspective view similar to FIG. 2 showing a third embodiment having yet another barrier configuration utilizing a band of stent material.

A second embodiment of a pouch 30 is shown in FIG. 5. The second embodiment differs from the first embodiment primarily in that a plurality of blades 32 are mounted to resilient ring 34. Blades 32 may be formed of a variety of materials, including those listed above for forming the pouch. The blades are outwardly biased using wire reinforcements or other biasing structure. Anchors 36 are preferably positioned in spaced-apart locations between the blades 32. The pouch 30 is sutured in place by attaching sutures between anchors 36 and adjacent tissue. The blades 32 spring outwardly into contact with surrounding tissue, thereby creating a seal or barrier against passage of food that might otherwise pass between gaps forming between anchor points.

Third Embodiment

FIG. 6 shows a third embodiment of a pouch 40, which uses an expandable stent-like band 42 for creating a seal or barrier. Band 42 is outwardly biased and may be formed of self-expanding material, such as stainless steel or a shape memory material such as nitinol or shape-memory polymer, and may be formed as a soft mesh or other framework formed of such materials in combination. The mesh may be created to have sufficiently small spaces between strands to form an effective barrier against a substantial portion of the ingested food, or it may be provided with a polymeric barrier that prevents ingested food from passing through the walls of the band 42. For example, the polymeric barrier may be a skin. formed on the exterior or interior of the mesh, or the mesh may be encapsulated in polymeric material or the polymer may be disposed in the interstices of the mesh.

During use, the pouch 40 is secured in place by attaching sutures between anchors 44 and adjacent tissue of the gastro-esophageal junction region. Band 42 then expands into contact with the surround tissue to form the seal or barrier. The band 42 is preferably positioned beyond the lower esophageal sphincter (identified as LES in FIG. 6) to avoid interference with proper sphincter function.

Fourth Embodiment

Figure 7:
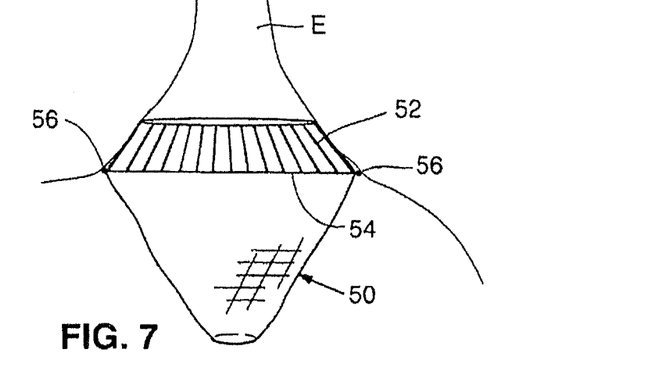
FIG. 7 is a perspective view similar to FIG. 2 showing a fourth embodiment having yet another barrier configuration utilizing leaf springs.

A fourth embodiment of a pouch 50, shown in FIG. 7, is similar to the previously described embodiments except that a plurality of leaf springs 52 are attached at the proximal end of the pouch. Springs 52 are outwardly biased to create the seal or barrier with surrounding tissue. As with prior embodiments, the pouch may include a resilient ring 54, and the pouch may be attached to surrounding tissue using sutures passed through anchors 56. In an alternative configuration, springs 52 may be coil springs which may be connected to a common structure at their proximal ends, or which may have free proximal ends.

Fifth Embodiment

Figure 8A:
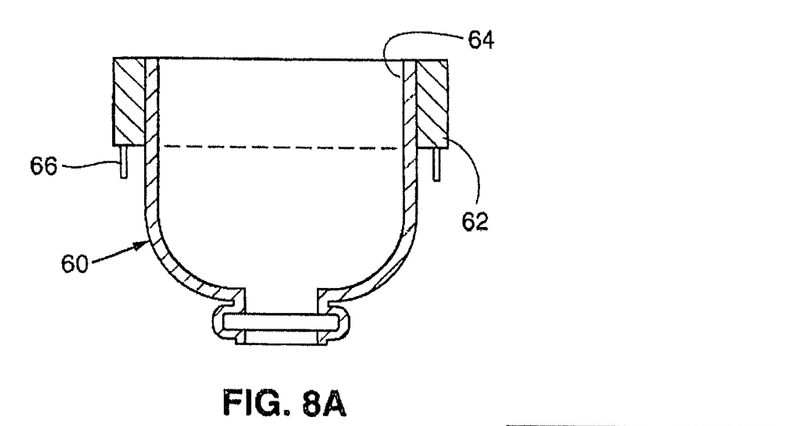
FIG. 8A is a cross-sectional side elevation view of a fifth embodiment of a pouch, which has a proximal rim that forms a circumferential seal with adjacent body tissue.
Figure 8B:
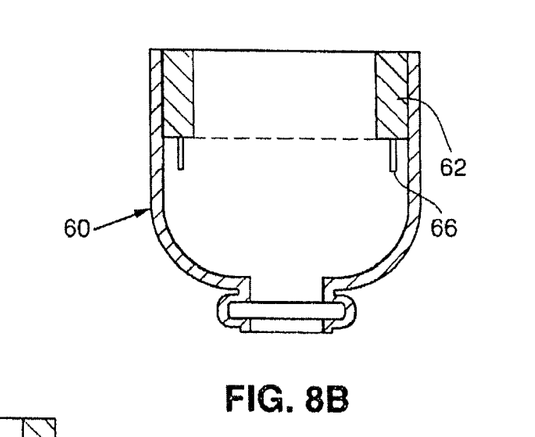
FIGS. 8B and 8C are cross-sectional side elevation views similar to FIG. 8A showing slight modifications to the rim position.
Figure 8C:
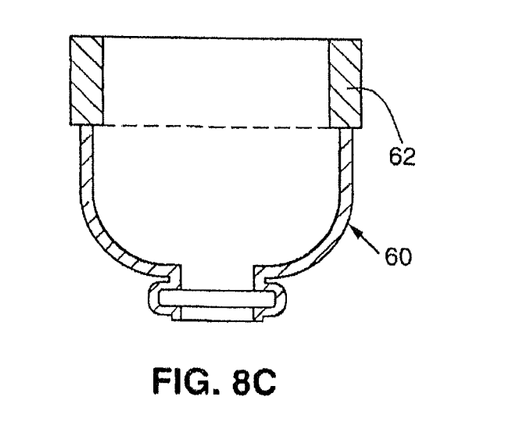
Figures 9A, 9B:
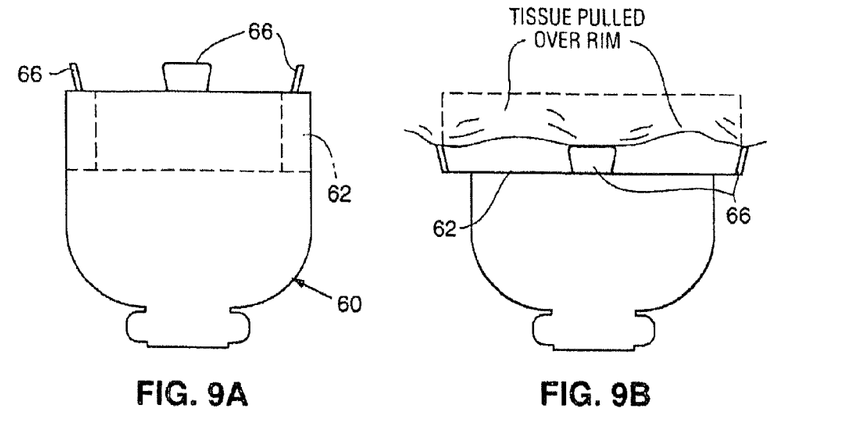
FIG. 9A is a side elevation view of the pouch of FIG. 8A, showing the rim in the inverted position.
FIG. 9B is a side elevation view similar to FIG. 9B, showing the rim moved to the non-inverted position and drawing tissue over a portion of the rim.

Referring to FIG. 8A, a fifth embodiment of a pouch 60 includes an enlarged rim 62 surrounding the proximal opening 64 of the pouch 60. Rim 62 may extend slightly outwardly from the external surface of the pouch as shown in FIG. 8A, or slightly inwardly as shown in FIG. 8B, or both as shown in FIG. 8C. In one form of the fifth embodiment, anchor loops 66 extend from a distal portion of the rim 62 as shown in FIG. 8A. Before the pouch 60 is fixed within the body, the rim 62 is inverted inside the pouch 60 to the position shown in FIG. 9A. Once the rim has been inverted, anchor loops 66 extend in a proximal direction as shown. The pouch 60 is inserted into the stomach and the anchor loops 66 are secured to tissue using sutures or other attachment means. Next, the rim 62 is returned to the non-inverted position shown in FIG. 9B, causing the anchor loops 66 to return to the distally-oriented position. The loops 66 pull the attached tissue in a distal direction, around the edges of the rim 62, creating a taut and leak-resistant seal around the rim.

Figure 10A:
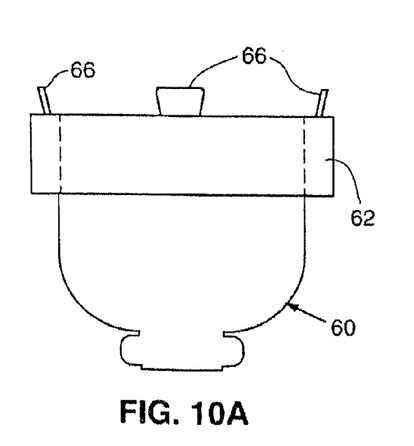
FIG. 10A is a side elevation view of an alternative to the pouch of FIG. 9A, showing the rim in an everted position.
Figure 10B:
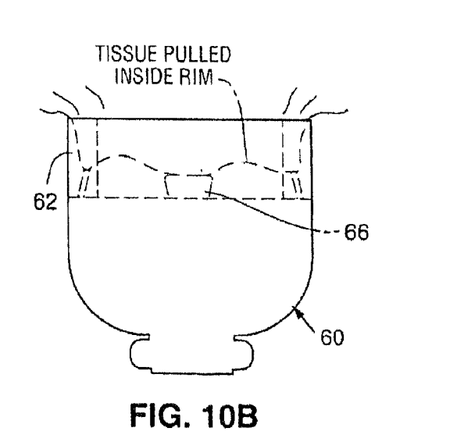
FIG. 10B is a side elevation view similar to FIG. 10B, showing the rim moved to the non-everted position and drawing tissue inside a portion of the rim.

In another form of the fifth embodiment, anchors 66 extend distally on an interior portion of the rim as shown in FIG. 8B. According to this form of the embodiment, before the pouch is fixed within the body, the rim 62 is everted outside the pouch 60 to the position shown in FIG. 10A—causing anchor loops 66 to extend in a proximal direction as shown. The pouch 60 is inserted into the stomach and the anchor loops 66 are secured to tissue using sutures or other attachment means. Next, the rim 62 is returned to the non-everted position shown in FIG. 10B, causing the anchor loops 66 to return to the distally-oriented position. The loops 66 pull the attached tissue in a distal direction, inside the edges of the rim 62, again creating a seal around the rim.

Sixth Through Eighth Embodiments

Figures 11, 12, 13:
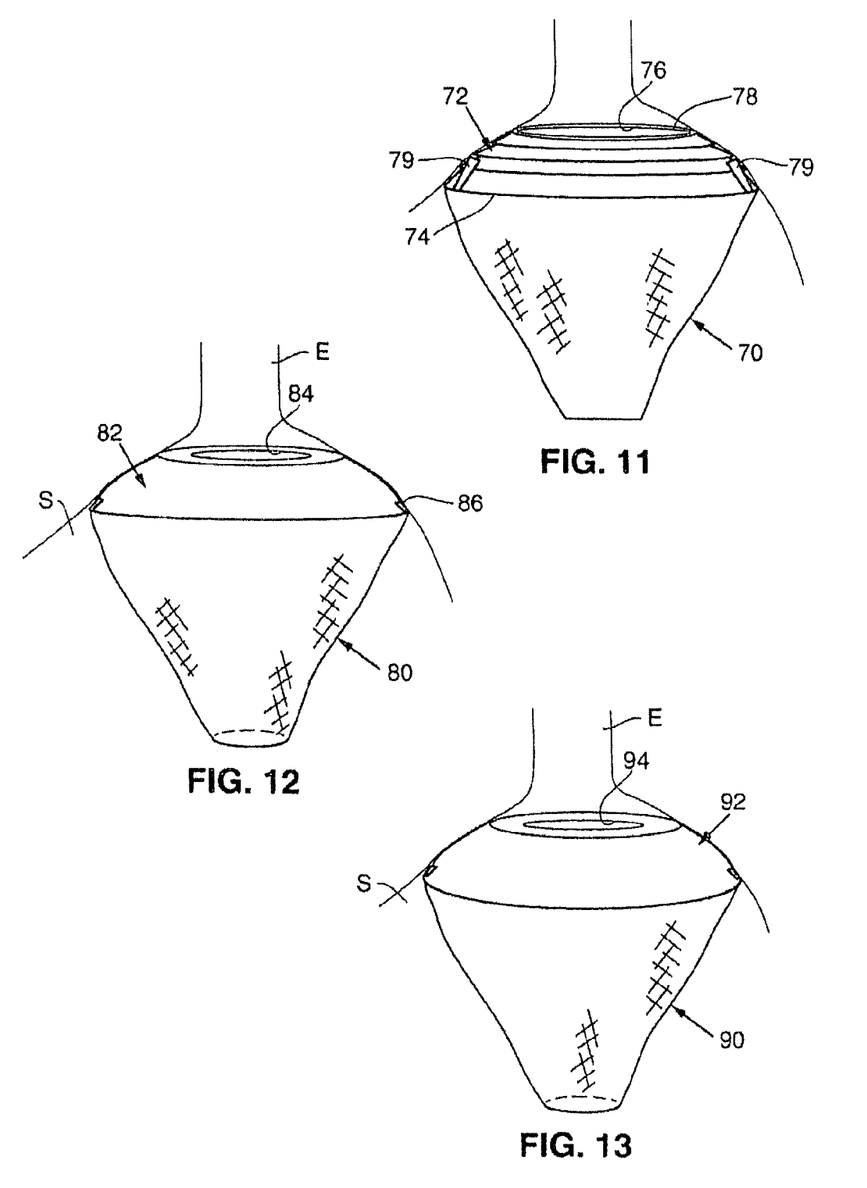
FIG. 11 is a schematic illustration showing a sixth embodiment of a pouch, which utilizes a bellows structure to create a barrier.
FIG. 12 is a schematic illustration showing a seventh embodiment of a pouch, which utilizes a conformable sealing ring.
FIG. 13 is a schematic illustration showing an eighth embodiment of a pouch, which utilizes an inflatable sealing ring.

FIG. 11 shows a sixth embodiment of a pouch 70, which includes an expandable bellows structure 72, attached to a resilient ring 74. Bellows structure 72 includes a central channel 76 in alignment with the proximal opening (not shown) of the pouch 70, and is preferably formed of a flexible material that is substantially impervious to masticated food, and may be formed of materials similar to those listed for use in constructing the pouch. It may have a substantially cylindrical shape or a tapered geometry such as that shown in FIG. 11. At the proximal end of the bellows structure 72, surrounding the central channel 76, is a sealing ring 78 formed of a flexible material capable of forming a seal when urged into contact with body tissue.

Anchors 79 are attached to resilient ring 74 and are used to receive sutures, clips, etc that will connect the pouch to surrounding body tissue. Once the pouch has been fixed within the stomach, the bellows structure 72 expands the sealing ring 78 into contact with surrounding tissue, thereby creating a barrier or seal. As with prior embodiments, the resilience of the bellows allows the seal to be maintained despite movement of the stomach or expansion of the pouch.

Similar embodiments are shown in FIGS. 12 and 13. In the seventh embodiment of FIG. 12, the proximal portion of the pouch 80 includes a conformable sealing ring 82 made of foam, sponge, silicone, or other conformable material that will seal against surrounding tissue when pressed into contact with the tissue. Ring 82 includes a central channel 84 and may include a cylindrical or tapered geometry. Anchors 86 receive sutures or clips used to fix the pouch to body tissue.

The eighth embodiment of FIG. 13 is a pouch 90 having a conformable sealing ring 92. Sealing ring 92 is formed of an elastic or inelastic bladder inflatable using an inflation fluid or gas. The bladder may be inflated prior to insertion into the stomach, or it may include a detachable inflation valve (not shown) that may be used to introduce inflation medium into the bladder after the pouch has been fixed within the stomach. As with the seventh embodiment, the sealing ring 92 may have a cylindrical or tapered geometry. Ingested food flows through a central channel 94 in the sealing ring 92 and into the pouch 90.

Ninth and Tenth Embodiments

Figure 14:
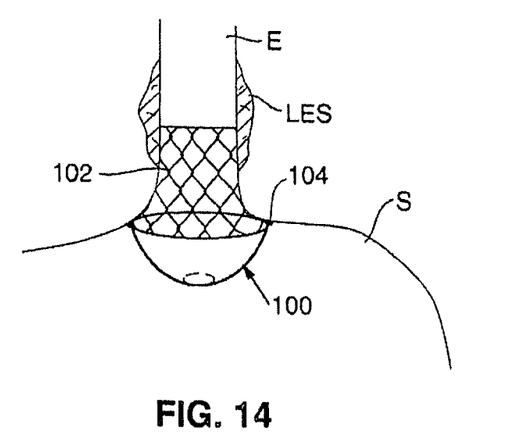
FIG. 14 is a schematic illustration showing a ninth embodiment of a pouch having an expandable barrier stent.
Figure 15:
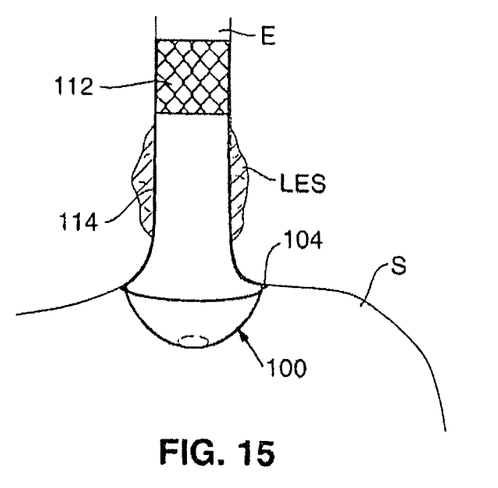
FIG. 15 is a schematic illustration shown a tenth embodiment of a pouch showing an alternative configuration of a barrier stent.

FIGS. 14 and 15 show ninth and tenth embodiments, respectively, of pouches having barrier devices for minimizing passage of food around, rather than through, the pouch. These embodiments are similar to the FIG. 6 embodiment in that they utilize a stent-like structure to expand against surrounding tissue to create the barrier or seal.

The barrier provided with the pouch 100 of FIG. 14 differs from that of FIG. 6 in that band 102 of stent material extends further into the esophagus, creating a seal with the tissue of the esophagus. This seal may be above, below, or within the lower esophageal sphincter (LES). As with each of the prior embodiments, anchors 104 receive sutures or clips that are used to fix the device to tissue in the region.

In the tenth embodiment shown in FIG. 15, a flexible tubular member 114 extends between the band 112 of stent material and the pouch 110. During use, member 114 may be positioned within the LES region while still preserving function of the LES.

Various embodiments of satiation devices have been described herein. These embodiments are given by way of example and are not intended to limit the scope of the present invention. It should be appreciated, moreover, that the various features of the embodiments that have been described may be combined in various ways to produce numerous additional embodiments. Also, while various materials, dimensions, shapes, implantation locations, etc. have been described for use with disclosed embodiments, others besides those disclosed may be utilized without exceeding the scope of the invention. Lastly, while the pouches have been described for use in controlling feelings of hunger, the barrier devices described herein may be equally suitable for use with other prosthetic devices positionable within the body, including prosthetic valves implanted in the lower esophagus or proximal stomach for controlling gastro-esophageal reflux disease (GERD).

We claim:

1. A method for treating a patient, comprising:
   introducing a prosthetic device into a lumen of the patient, wherein the prosthetic device includes: a) a barrier extending from a proximal edge at a proximal end of the prosthetic device to a distal base defined by a resilient ring, the resilient ring being positioned distal to the proximal end of the prosthetic device, wherein the barrier includes an outwardly biased circumferential band, and b) a self-expandable wall extending from a proximal opening defined by the resilient ring to a distal opening at a distal end of the prosthetic device, wherein the distal opening is smaller than the proximal opening;
   transforming at least a portion of the barrier from a first configuration to a second configuration radially outward relative to the first configuration to cause the barrier to contact tissue defining the lumen, wherein during the transforming the distal base of the barrier remains fixed to the resilient ring and the proximal edge of the barrier moves relative to the wall; and
   securing the prosthetic device to tissue defining the lumen.

2. A method for treating a patient, comprising:
   introducing a prosthetic device into a lumen of the patient, wherein the prosthetic device includes a barrier and a wall extending from a proximal opening adjacent the barrier to a distal opening, wherein:
      the wall defines a passage,
      the barrier extends around a circumference of the proximal opening, and the distal opening is smaller than the proximal opening; and
   transforming at least a portion of the barrier from a first configuration to a second configuration radially outward relative to the first configuration to cause the barrier to contact tissue of the lumen, wherein transforming includes allowing the barrier to pivot relative to a ring defining the proximal opening,
   wherein the lumen is at least one of an esophagus and a stomach.

3. The method of claim 2, wherein the wall includes a flexible material.

4. The method of claim 2, wherein the wall is self-expanding.

5. The method of claim 2, wherein the wall includes a flexible material and at least one supporting member, wherein the at least one supporting member includes at least one of a soft mesh, a cage structure, a rib, or a ring.

6. The method of claim 2, wherein the step of transforming includes allowing the barrier to self-expand.

7. The method of claim 2, wherein the ring is resilient.

8. The method of claim 2, further comprising securing the prosthetic device to tissue of the lumen.

9. A method for treating a patient, comprising:
   introducing a prosthetic device into a lumen of the patient, wherein the prosthetic device includes a) a barrier secured to a resilient ring and extending proximally from the resilient ring, and b) a wall secured to the resilient ring and extending distally from the resilient ring from a proximal opening to a distal opening, wherein:
   the wall defines a passage,
   the barrier extends around a circumference of the proximal opening, and
   the distal opening is normally open and is smaller than the proximal opening;
   transforming a proximal end of the barrier from a first configuration to a second configuration radially outward relative to the first configuration to cause the barrier to contact tissue of the lumen;
   securing the prosthetic device to tissue of the lumen of the patient; and
   allowing food to pass through the passage.

10. The method of claim 9, wherein the lumen is at least one of an esophagus and a stomach.

11. The method of claim 9, wherein the barrier is biased in a radially outward direction.

12. The method of claim 9, wherein the barrier includes an inflatable bladder.

13. The method of claim 9, wherein the step of securing includes suturing the prosthetic device to tissue of the lumen.

* * * * *